(12) United States Patent
DeToro et al.

(10) Patent No.: US 6,302,858 B1
(45) Date of Patent: Oct. 16, 2001

(54) COMPOUND ADJUSTABLE ANKLE FOOT ORTHOSIS BRACE

(75) Inventors: William DeToro, Poland; Brian Perala, Geneva, both of OH (US)

(73) Assignee: Anatomical Concepts, Inc., Youngstown, OH (US)

( * ) Notice: Subject to any disclaimer, the term of this patent is extended or adjusted under 35 U.S.C. 154(b) by 0 days.

(21) Appl. No.: 09/696,657

(22) Filed: Oct. 26, 2000

(51) Int. Cl.[7] ........................................ A61F 5/00
(52) U.S. Cl. .................... 602/5; 602/23; 602/27
(58) Field of Search .................... 128/846, 869, 128/882; 602/5, 23, 27, 28

(56) References Cited

U.S. PATENT DOCUMENTS

| | | |
|---|---|---|
| 5,088,479 | 2/1992 | DeToro . |
| 5,431,624 | 7/1995 | Saxton et al. . |
| 5,486,157 | 1/1996 | DiBenedetto . |
| 5,545,127 | 8/1996 | DeToro . |
| 5,593,383 | 1/1997 | DeToro . |
| 5,908,398 | 6/1999 | DeToro . |
| 5,944,679 | 8/1999 | DeToro . |

*Primary Examiner*—Michael A. Brown
(74) *Attorney, Agent, or Firm*—Harpman & Harpman

(57) ABSTRACT

An ankle and foot orthosis brace for use in supporting an immobilization of a patient's ankle and foot. The brace is of a multi-part L-shaped configuration with a contoured leg support portion and a foot portion interconnected by an incrementally hinge and lateral bearing assembly therebetween. A foot pad with an apertured tab extends therefrom and is part of the foot portion with adjustable fabric fasteners extending from both the foot portion, apertured tabs and the leg support portion secured to the brace to the patient's leg and foot.

7 Claims, 7 Drawing Sheets

COMPOUND ADJUSTABLE ANKLE FOOT ORTHOSIS BRACE

BACKGROUND OF THE INVENTION

1. Technical Field

The present invention relates to therapeutic leg and foot braces more particular to a securing apparatus having a footpad, a fabric foot engagement enclosure for releasably securing the brace to the foot and ankle of the patient and to maintain a consistent pressure against the foot, sole and ankle of the patient for therapeutic purposes.

2. Description of Prior Art

An orthotic foot and ankle brace typically has an L-shaped construction with a contoured leg support portion, a foot portion, and an interconnecting heel portion connected therebetween. An integral fabric foot engagement enclosure is provided to secure the brace to the patient's foot and ankle.

Prior art devices of this type provide for a variety of leg, ankle and foot stabilization utilizing two-part brace assemblies interconnected by free hinges of elastomeric material as seen in U.S. Pat. No. 5,496,263 that permit the tolocural articulation to move about a single axis.

Other prior art patents, such as U.S. Pat. No. 5,431,624 disclose leg and foot braces having adjustable angles between the two sections with an extended ground engagement sole and a cam action locking assembly.

U.S. Pat. No. 5,486,157 discloses a hinge at the apex of a contoured heel portion to provide free dorsiflexion and plantar flexion with a pivot point below the hinges for inversion, eversion, pronation and supination of the foot.

Other therapeutic foot devices can be seen in U.S. Pat. No. 5,431,624 in which an ankle controlling section slidably attaches to a foot supporting section so that the angle between the two sections can be changed and flexed to a wearer's foot in the desired manner.

Applicant's own U.S. Pat. Nos. 5,088,479, 5,545,127, 5,593,383, 5,908,398 and 5,944,679 define the present state of the art in ankle and foot orthosis beginning with the resilient L-shaped construction in U.S. Pat. No. 5,088,479, the introduction of a laterally adjustable ankle and foot orthosis in U.S. Pat. No. 5,545,127 and adjustable ankle and foot orthosis brace having an adjustable hinge assembly between the leg configuration and the heel configuration in U.S. Pat. No. 5,908,398 and various foot enclosure mechanisms set forth in relation to foot pads and leg engagement sections.

SUMMARY OF THE INVENTION

An ankle and foot orthosis device for supporting and selectively immobilizing a patient's ankle and foot having both adjustable lateral angular inclination with dorsiflexion and plantar flexion motion or static position. The orthotic brace generally comprises a leg portion, a foot portion and an interconnecting heel portion with a unique intermedial transition portion with adjustable multi-angular bearing surfaces to input selective angular inclination both bi-laterally and dorsi/plantar flexion by respective multiple overlapping intermedial end portions of respective resilient interconnecting portions.

OBJECTS AND ADVANTAGES

Accordingly, it is the object of the present invention to provide an incremental adjustable limit of bi-lateral angular inclination and imputable limited degrees of plantar flexion and dorsiflexion in the sagitial plane. An intermedial transition element provides a mechanical interface between adjacent input portions while maintaining resilient interplay between the leg and foot portions of the orthosis device.

DESCRIPTION OF THE PREFERRED EMBODIMENT

Figure 1:
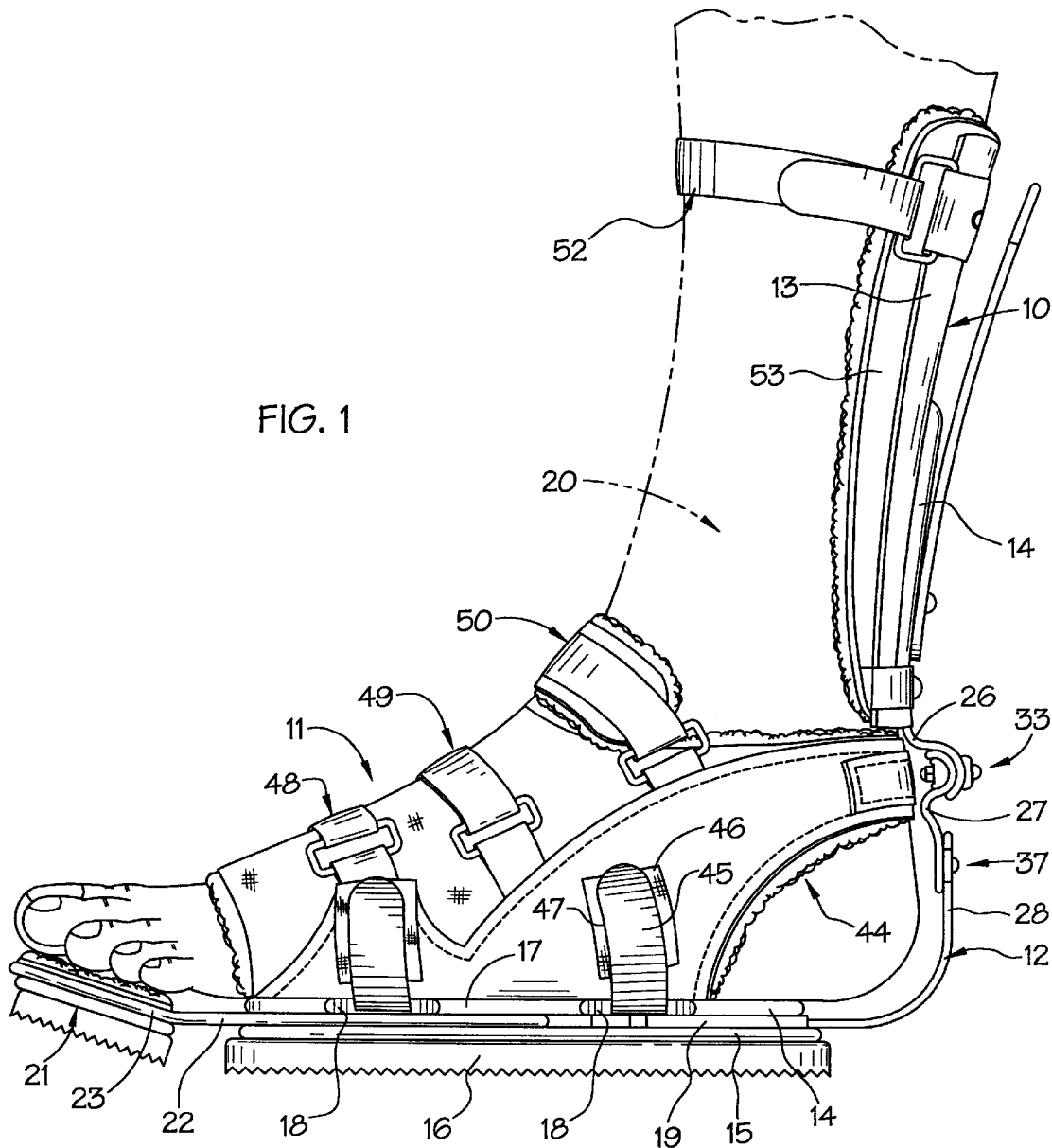
FIG. 1 is a side elevational view of the present invention.
Figure 2:
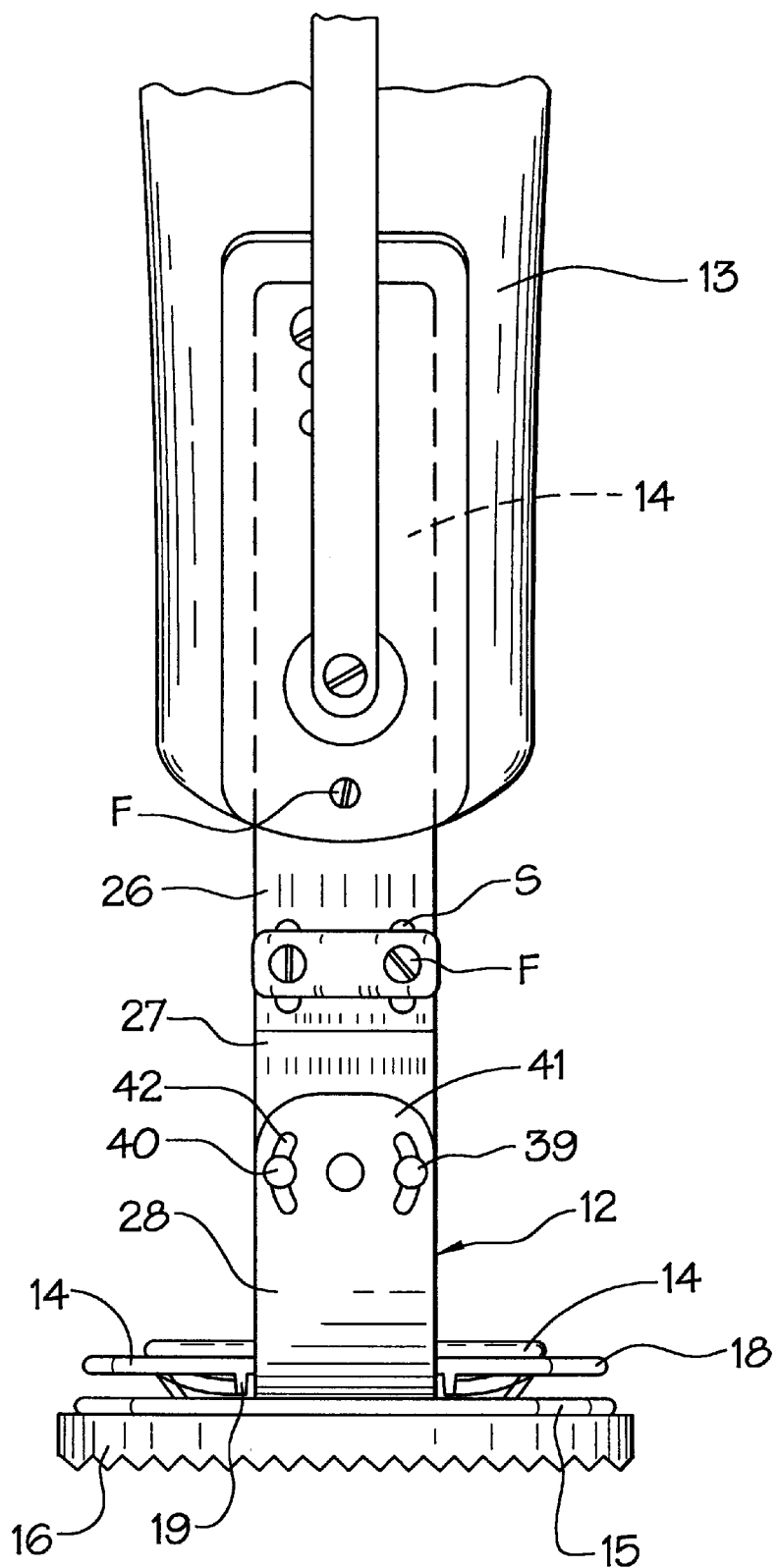
FIG. 2 is a rear elevational view thereof.
Figure 3:
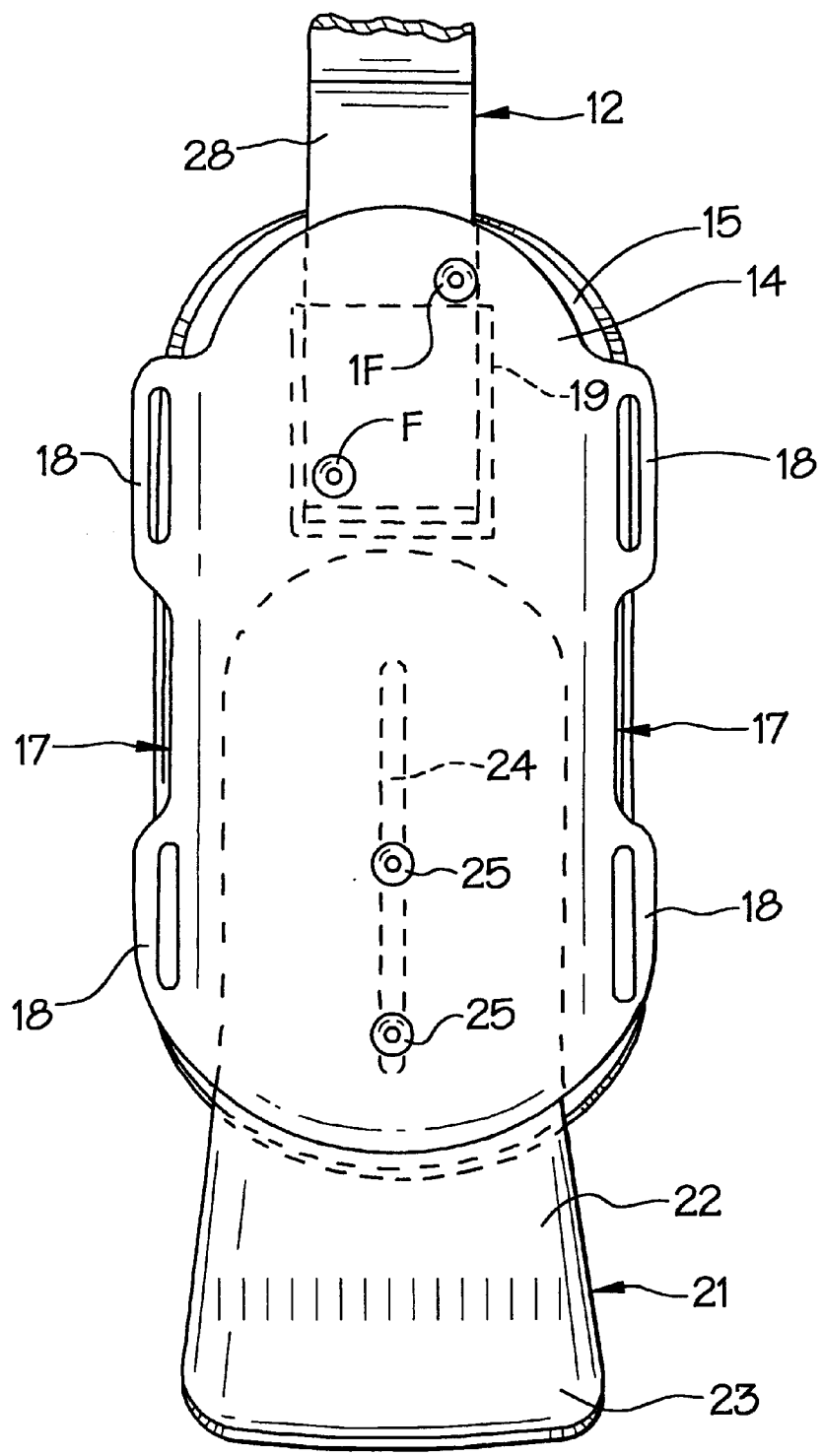
FIG. 3 is a top plan view of the foot portion of the invention with portions broken away.

Referring to FIGS. 1 and 2 of the drawings, an ankle and foot orthosis brace of the invention can be seen comprising, a leg portion 10, a foot portion 11 and an interconnecting heel portion 12 extending therebetween. The leg portion 10 has an enlarged transversely contoured leg support 13 having a recessed channel 14 formed inwardly from one end thereof. The foot portion has a footpad 14 connected to a generally rectangular attachment brace 15. The attachment brace 15 has a resilient walking pad 16 secured thereto. The foot pad 14 is also of a generally rectangular configuration with an area of reduced transverse dimension at 17 defining pairs of longitudinally spaced apertured tabs 18, as best seen in FIG. 3 of the drawings. A mounting bracket 19 extends inwardly from the bottom of the footpad 14 for engagement of the interconnecting heel portion 12 between the footpads 14 and abutting attachment base 15. In practice, the leg and foot portions are made of synthetic plastic resin material so that they can be molded or preformed to the desired contours required for engagement with a patient's leg 20 shown in broken lines, as best seen in FIG. 1 of the drawings.

A toe extension member 21 can be seen in FIGS. 1–3 of the drawings and is adjustably secured to the footpad 15 opposite the mounting bracket 19. The toe extension member 21 has a flat base area 22 with an upturned angular offset end portion 23. The toe extension 21 is registerably attached between the footpad 17 and the attachment base 15 by a mounting slot 24 aligned for registration with adjustable fasteners 25 extending from said footpad 15 through the attachment base 15 allowing for the lengthening of the overall foot portion 11.

Figure 6:
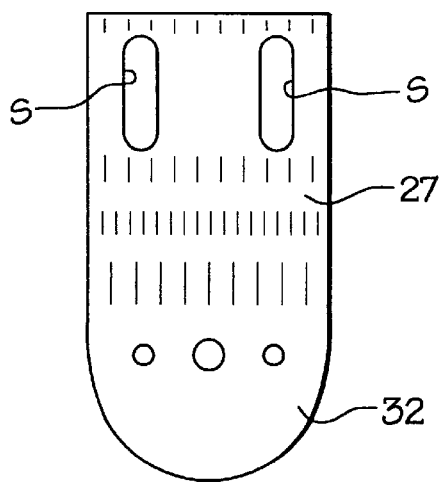
FIG. 6 is a rear elevational view of intermedial transition element defining both its support bearing surface and a bearing element for respective adjustment portions.
Figure 7:
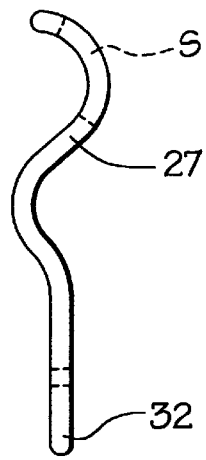
FIG. 7 is an enlarged side elevational view of the intermedial transition element shown in FIG. 6.
Figure 8:
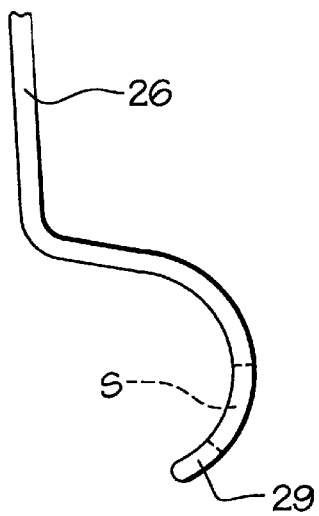
FIG. 8 is an enlarged side elevational view of the hinge engagement distal end of the leg support portion.
Figure 9:
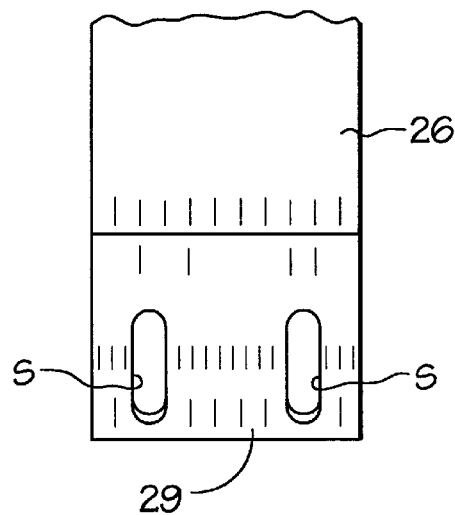
FIG. 9 is an enlarged rear elevational view of the hinge engagement portion shown in FIG. 8.
Figure 10:
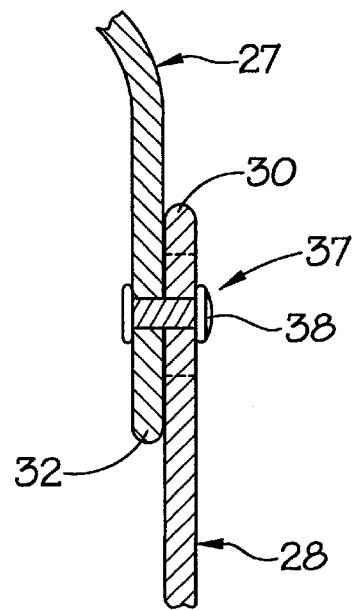
FIG. 10 is an enlarged cross-sectional view of the hinge engagement portion on lines 10—10 of FIG. 5.

The interconnecting heel portion 12 comprises an upper leg element 26, an intermediate bearing engagement element 27 and a lower foot engagement element 28, all of which are comprised of a resilient metal alloy or suitable material. The upper leg element 26 is secured within the recessed channel 14 of the leg support 13 by multiple fasteners F and has an articulated curved free end at 29. The foot element 28 extends from and is secured within the mounting bracket 19 of the foot pad 15 by a pair of fasteners F that interengage therethrough in registration with selective fixed apertures in the mounting bracket 19, as best seen in FIG. 3 of the drawings. The foot engagement 28 has an apertured free end at 30. The intermediate bearing engagement element 27 has an articulated upper curved end at 31 with transversely spaced longitudinal slots S within and an oppositely disposed apertured pivot engagement end 32 as best seen in FIGS. 6, 7 and 10 of the drawings.

A hinge assembly 33 is formed by the respective overlapping articulated free ends 29 and 31 with a hinge block 34 registerable within the arcuate upper contoured free end 31 of the intermedial bearing engagement element 27 and correspondingly a compression cap fitting 35 with a curved interengagement surface 36 is positioned over the aligned slots S in the articulated curved free end 29 of the leg element 26 in oppositely disposed aligned relation to the hinge block 34. The hinge block 34 and compression cap fitting 35 are registerably secured together by a pair of threaded fasteners F extending through aligned apertures therein and the corresponding aligned slots S of the respective upper leg element 26 and intermedial bearing engagement element 27 and threadably engaged by lock nuts 36A.

Figure 4:
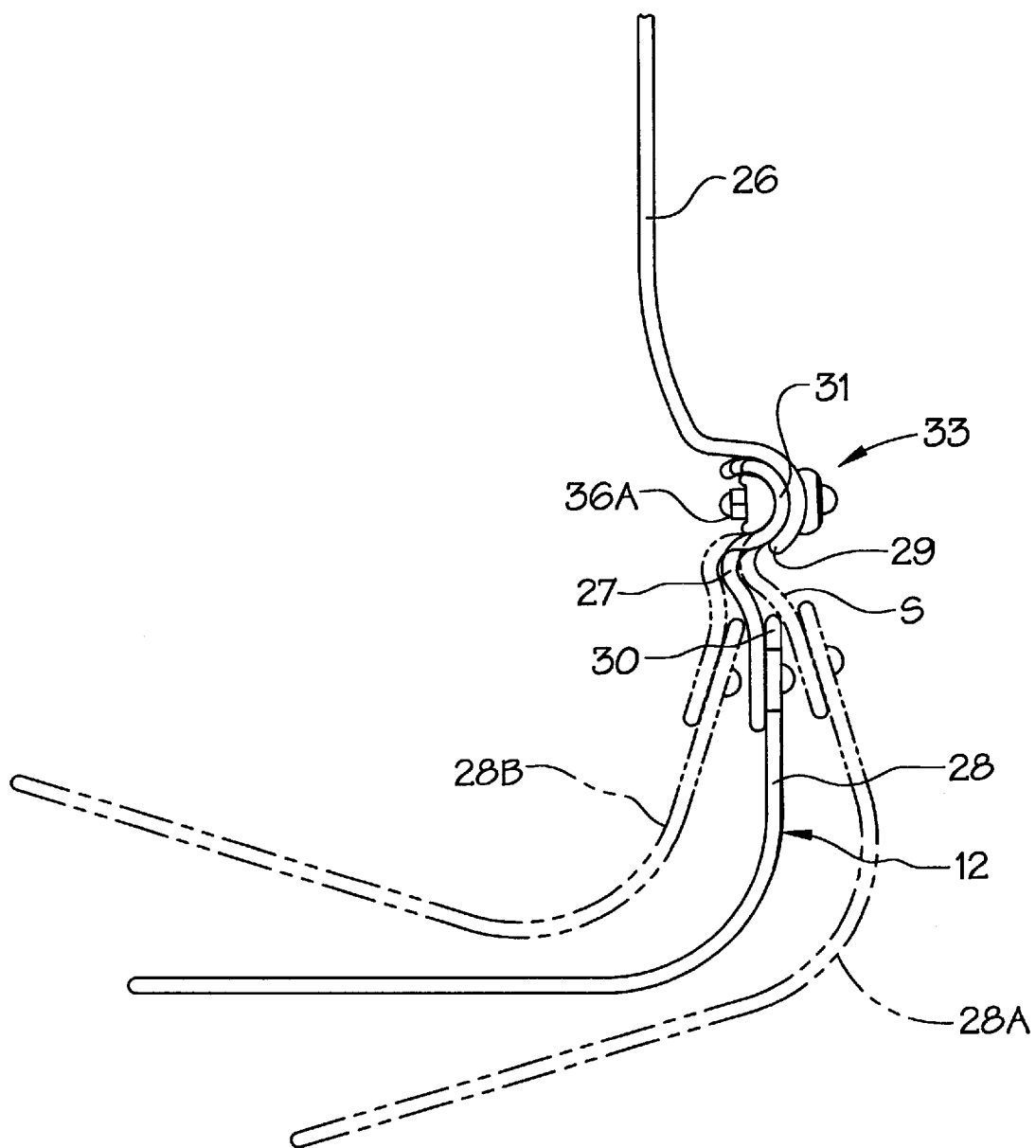
FIG. 4 is a side elevational view of the hinge and bi-later adjustment element with hinge range of motion illustrated in broken lines of the foot engagement portion.
Figure 5:
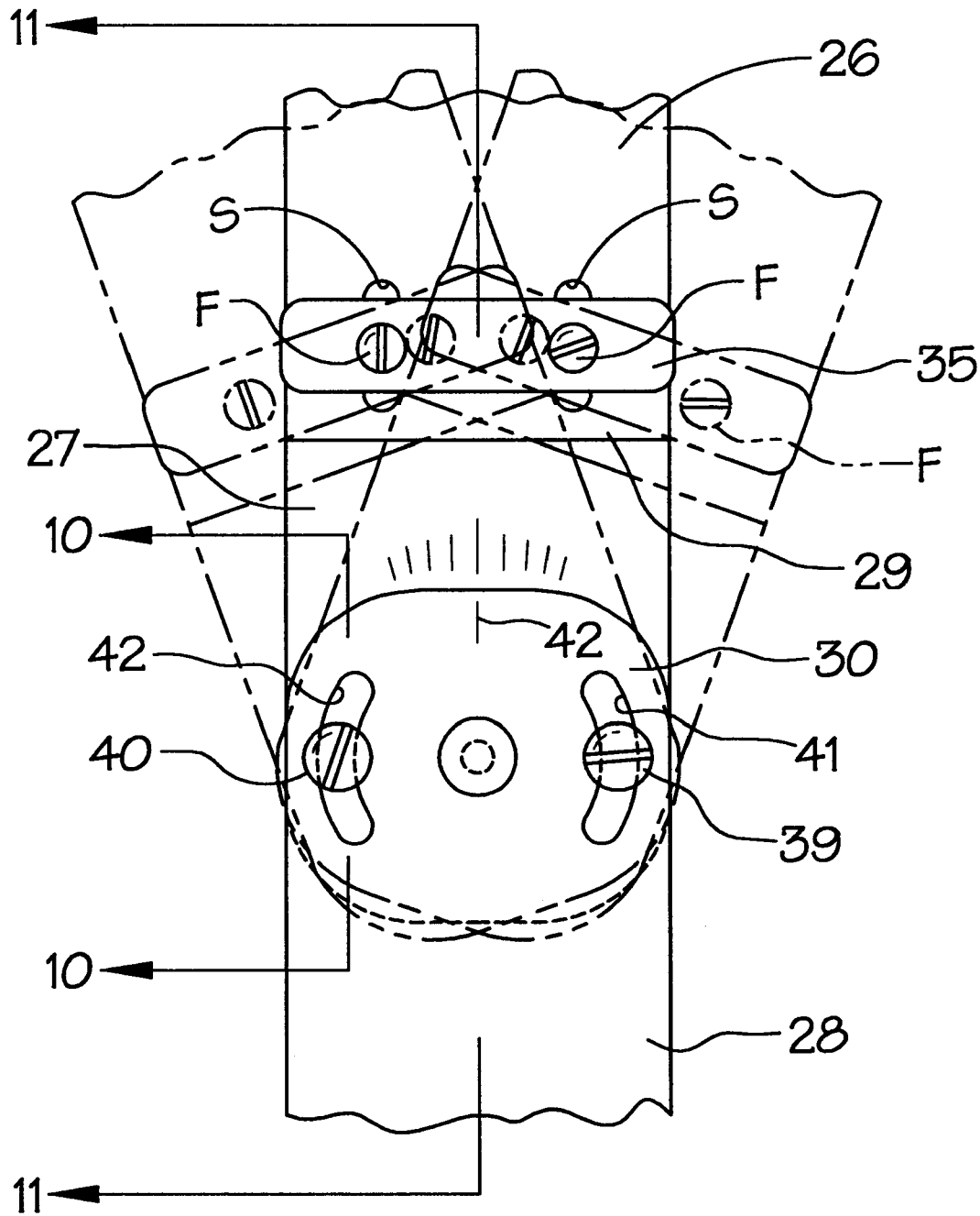
FIG. 5 is an enlarged partial rear elevational view of the hinge and lateral adjustment elements illustrating the bi-lateral range of motion imparted to the leg engagement portion in broken lines.
Figure 11:
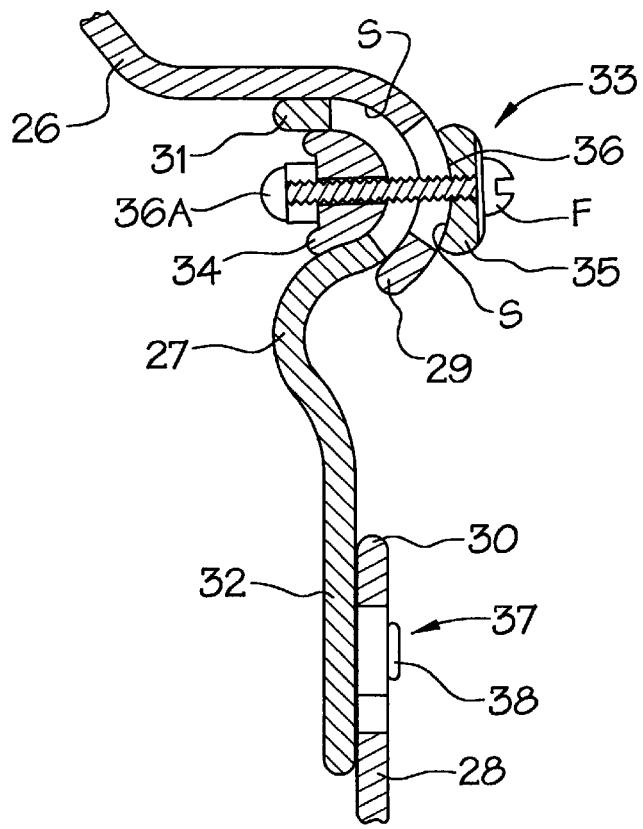
FIG. 11 is a cross-sectional view of lateral adjustment portion on lines 11—11 of FIG. 5.

Referring now to FIGS. 4 and 5 of the drawings, the respective overlapping apertured curved free end 30 of the foot engagement element 28 and the apertured pivot engagement end 32 of the intermedial bearing engagement element 27 define a main pivot fitting 37. Accordingly, a pivot pin 38 interconnects said respective overlapping pivot ends 30 and 32 extending through centrally positioned respective and aligned apertures therein as best seen in FIG. 11 of the drawings. A pair of oppositely disposed limit stop fasteners 39 and 40 are threadably secured into registering threaded apertures in the pivot engagement end 32 of the intermediate bearing engagement element 27 through respective aligned arcuate slots 41 and 42 in the overlapping free end portion 30 of the foot engagement element 28, best seen in FIGS. 10 and 11 of the drawings.

In use, the intermedial bearing engagement element 27 can be disposed laterally in relation to the foot engagement element 28 as illustrated in solid and broken lines in FIG. 5 of the drawings. The degree of lateral movement therebetween can be incrementally adjustably achieved by alignment of an indicator groove 42 on the pivot engagement end 32 of the intermedial bearing engagement element 27 in initial vertical alignment with the central pivot pin and multiple incrementally spaced indicator grooves 43 formed on the free end 30 of the foot engagement portion 28 so as to be selectively aligned therewith.

Once the desired degree of lateral alignment is achieved, the stop limit fasteners 39 and 40 are secured locking the so aligned overlapping pivot engagement end 32 of the intermedial bearing engagement element 27 and the free end 30 of the foot engagement portion 28 together.

Referring now to FIG. 4 of the drawings, the hereinbefore described hinge assembly 33 can be seen allowing an effective range of motion of the foot portion 11, not shown, in relation to the leg element 13 delineated by broken lines at 28A and 28B of the foot engagement element 28 and is limited thereto.

It will also be seen that the adjustable range of movement of the foot element 28 so illustrated is limited to the interengagement of the hereinbefore described arcuate free ends at 29 and 31.

Referring back now to FIG. 1 of the drawings, it will be seen that the foot portion 11 is illustrated comprising a fabric foot engagement enclosure 44 that is removably secured to the foot pad 14 by a plurality of attachment strips 45 that extend from the foot engagement enclosure 44 extending through the respective apertured tabs 18 and back against themselves at 46 by interlocking hook and loop material inserts 47 thereon.

Secondary enclosure straps and buckle assemblies 48, 49 and 50 provide for overlapping closure of the foot engagement enclosure 44. Leg attachment straps assemblies 51 and 52 are secured to and extend from the leg portion 13 adjacent its respective upper and lower free ends. A leg attachment strap areas 51 and 52 secure the patient's upper leg L shown in broken lines to a fabric pad 53 secured independently to the leg portion 13 by the use of hook and loop fasteners as hereinbefore described.

It will be apparent from the above description that the present invention provides for the static accommodation of a patient's particular range of dorsiflexion and plantar flexion motion and the incremental adjustment degree of lateral angular inclination by use of the hereinbefore described composite hinge and bi-lateral pivot assembly.

It will be apparent to those skilled in the art that various changes and modifications may be made therein without departing from the spirit of the invention.

What is claimed is:

1. A therapeutic leg and foot brace for use on a patient comprising, a foot portion connected to a leg portion by a compound resilient joint assembly, said foot portion having a rigid foot pad, a foot engagement enclosure releasably secured to said foot pad, said compound resilient joint assembly comprises, an upper leg element, an intermedial bearing element and a pivot bearing element, an end of said upper leg element is adjustably engaged with an end of said intermedial bearing element wherein said engaging ends have substantially a C-shaped, each of the C-shaped overlapping end portions having elongated openings registerably aligned with one another and an apertured locking assembly interengaged thereon, said pivot bearing element and said intermedial bearing element having overlapping free end portions being movable with respect to one another laterally, a pivot and bearing means mounted through said areas of overlap pivotally securing said pivot bearing element and said intermedial bearing element to one another, a first and second arcuate bearing surface means formed in the free end of said pivot bearing element, a first and second limit stop means secured to said pivot bearing element within said first and second arcuate bearing surface means respectively, said first and second arcuate bearing surface means including a curved edge surface having identical radius.

2. The therapeutic leg and foot brace set forth in claim 1 wherein said aperture locking assembly comprises, an apertured hinge block and an apertured compression cap, the apertured compression block being in aligned relationship with said apertured hinge block, fasteners extending through the aperture of said hinge block and compression cap and through the opening in each of said overlapping end portions.

3. The therapeutic leg and foot brace set forth in claim 1 wherein said pivot and bearing means for pivotally securing said pivot bearing element and said intermedial bearing element comprises a pivot pin.

4. The therapeutic leg and foot brace set forth in claim 1 wherein said first and second limit stop means secured to said respective arcuate bearing surface means comprises, threaded fasteners adjustably engaged within registerably threaded apertures in said intermedial bearing element.

5. The therapeutic leg and foot brace set forth in claim 1 wherein said foot portion further comprises an attachment brace, a resilient walking pad secured to said attachment brace and an adjustable toe extension extensively positioned in relation thereto.

6. The therapeutic leg and foot brace set forth in claim 1 wherein said pivot-bearing element secured to said foot portion is preferably made of resilient metal material.

7. The therapeutic leg and foot brace set forth in claim 1 wherein said intermedial bearing element is preferably made of resilient metal material.

* * * * *